United States Patent
Lee et al.

(10) Patent No.: US 9,030,187 B2
(45) Date of Patent: May 12, 2015

(54) NANOGAP DEVICE AND METHOD OF PROCESSING SIGNAL FROM THE NANOGAP DEVICE

(71) Applicant: Samsung Electronics Co., Ltd., Suwon-Si, Gyeonggi-Do (KR)

(72) Inventors: Chang-seung Lee, Yongin-si (KR); Yong-sung Kim, Namyangju-si (KR); Jeo-young Shim, Yongin-si (KR); Joo-ho Lee, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 220 days.

(21) Appl. No.: 13/856,026

(22) Filed: Apr. 3, 2013

(65) Prior Publication Data

US 2014/0125310 A1   May 8, 2014

(30) Foreign Application Priority Data

Nov. 5, 2012   (KR) .......................... 10-2012-0124464

(51) Int. Cl.
| | |
|---|---|
| *G01N 27/00* | (2006.01) |
| *G01R 27/08* | (2006.01) |
| *G01N 33/487* | (2006.01) |
| *B82Y 15/00* | (2011.01) |
| *G01N 15/12* | (2006.01) |
| *G01N 27/327* | (2006.01) |

(52) U.S. Cl.
CPC .............. *B82Y 15/00* (2013.01); *Y10S 977/734* (2013.01); *Y10S 977/938* (2013.01); *G01N 15/1227* (2013.01); *G01N 27/3271* (2013.01); *G01N 33/48721* (2013.01)

(58) Field of Classification Search
CPC .................. G01N 33/48721; G01N 33/48707; G01N 33/487; G01N 33/48; G01N 33/4836; G01N 15/12; G01N 15/1227; B82Y 15/00; Y10S 977/938; Y10S 977/734

USPC .................. 324/71.1, 692; 204/400, 403.01; 977/700, 701, 712, 723, 734
See application file for complete search history.

(56) References Cited

U.S. PATENT DOCUMENTS

| | | |
|---|---|---|
| 7,678,357 B2 | 3/2010 | Watanabe et al. |
| 2011/0168562 A1* | 7/2011 | Nuckolls et al. .............. 204/600 |

(Continued)

FOREIGN PATENT DOCUMENTS

| | | |
|---|---|---|
| KR | 10-0849384 B1 | 7/2008 |
| KR | 2008-0110169 A | 12/2008 |
| KR | 2010-0001062 A | 1/2010 |
| KR | 2011-0036204 A | 4/2011 |

(Continued)

OTHER PUBLICATIONS

P. Xie et al. "Local electrical potential detection of DNA by nanowire-nanopore sensors"; Macmillan Publishers; Nature Nanotechnology vol. 7, Feb. 2012.

*Primary Examiner* — Hoai-An D Nguyen
(74) *Attorney, Agent, or Firm* — Harness, Dickey & Pierce, P.L.C.

(57) ABSTRACT

A nanogap device includes a first insulation layer having a nanopore formed therein, a first nanogap electrode which may be formed on the first insulation layer and may be divided into two parts with a nanogap interposed between the two parts, the nanogap facing the nanopore, a second insulation layer formed on the first nanogap electrode, a first graphene layer formed on the second insulation layer, a first semiconductor layer formed on the first graphene layer, a first drain electrode formed on the first semiconductor layer, and a first source electrode formed on the first graphene layer such as to be apart from the first semiconductor layer.

19 Claims, 10 Drawing Sheets

(56) References Cited

U.S. PATENT DOCUMENTS

2011/0217763 A1 9/2011 Rasooly et al.
2011/0278535 A1 11/2011 DeHeer
2014/0062454 A1* 3/2014 Jeon et al. .................... 324/71.1

FOREIGN PATENT DOCUMENTS

| KR | 2011-0129528 A | 12/2011 |
| KR | 2012-0000343 A | 1/2012 |
| WO | WO-2011/123513 A1 | 10/2011 |

* cited by examiner

NANOGAP DEVICE AND METHOD OF PROCESSING SIGNAL FROM THE NANOGAP DEVICE

CROSS-REFERENCE TO RELATED APPLICATIONS

This application claims priority under 35 U.S.C. §119 to Korean Patent Application No. 10-2012-0124464, filed on Nov. 5, 2012, in the Korean Intellectual Property Office, the disclosure of which is incorporated herein in its entirety by reference.

BACKGROUND

1. Field

Example embodiments relate to nanogap devices and/or methods of processing signals from the nanogap devices.

2. Description of the Related Art

Various methods have been developed to detect a target biomolecule such as a DNA (deoxyribonucleic acid) from a sample. Among them, a method using a nanogap has been highlighted as a highly-sensitive DNA detection system.

At present, a system for measuring a tunneling current or a blockade current when a DNA, a ribonucleic acid (RNA), or the like passes through a nanogap is implemented variously. Signal detection may be difficult because a molecule passes through a nanogap very fast and a signal from the nanogap is small. For example, since DNA may move at an ultrahigh speed of $10^7$ base/sec or higher, existing electrical signal detecting methods may have difficulty in distinguishing four different DNA bases having an interval of 0.37 nm.

SUMMARY

Example embodiments relate to nanogap devices and/or signal processing methods using the nanogap devices.

Additional aspects will be set forth in part in the description which follows and, in part, will be apparent from the description, or may be learned by practice of example embodiments.

According to example embodiments, a nanogap device includes a first insulation layer having a nanopore formed therein, a first nanogap electrode which is formed on the first insulation layer and is divided into two parts with a nanogap interposed between the two parts, the nanogap facing the nanopore, a second insulation layer formed on the first nanogap electrode, a first graphene layer formed on the second insulation layer, a first semiconductor layer formed on the first graphene layer, a first drain electrode formed on the first semiconductor layer, and a first source electrode formed on the first graphene layer such as to be apart from the first semiconductor layer.

In example embodiments, portions of the two parts of the first nanogap electrode that face the nanogap may be narrower than the other portions.

In example embodiments, a thickness of the first nanogap electrode may be 1 nm or less.

In example embodiments, a length of the nanogap of the first nanogap electrode may be 2 nm or less.

In example embodiments, the first nanogap electrode may include a graphene material.

In example embodiments, the nanogap device may further include a first protection layer that covers the first graphene layer, the first semiconductor layer, and the first drain electrode, a second nanogap electrode which may be formed on the first protection layer and may be divided into two parts with a nanogap facing the nanopore and interposed between the two parts, a third insulation layer formed on the second nanogap electrode, a second graphene layer formed on the second insulation layer, a second semiconductor layer formed on the second graphene layer, a second drain electrode formed on the second semiconductor layer, and a second source electrode formed on the second graphene layer such as to be apart from the second drain electrode.

In example embodiments, portions of the two parts of the second nanogap electrode that face the nanogap may be narrower than the other portions.

In example embodiments, a thickness of the second nanogap electrode may be 1 nm or less.

In example embodiments, a length of the nanogap of the second nanogap electrode may be 2 nm or less.

In example embodiments, the second nanogap electrode may include a graphene material.

In example embodiments, the nanogap device may further include a substrate having a hole formed therein, and the first insulation layer may be formed on the substrate so that the nanopore faces the hole of the substrate.

In example embodiments, the hole may have an inclined side surface and may narrow from an entrance to an inside of the hole.

According to example embodiments, a method of processing a signal from a nanogap device includes arranging a plurality of the above-described nanogap devices such that respective nanogaps of the plurality of nanogap devices face one another, measuring a drain current signal between the first drain electrode and the first source electrode of each of the plurality of nanogap devices according to time, and synchronizing the respective drain current signals of the plurality of nanogap devices with one another In example embodiments, the method may further include summing the synchronized drain current signals of the plurality of nanogap devices to obtain an amplification signal or obtaining an error signal from a difference between the synchronized drain current signals of the plurality of nanogap devices.

According to example embodiments, a method of processing a signal from a nanogap device includes measuring a first drain current signal between the first drain electrode and the first source electrode according to time, and measuring a second drain current signal between the second drain electrode and the second source electrode according to time.

In example embodiments, the method may further include synchronizing the first drain current signal with the second drain current signal. The method may further include obtaining an amplification signal from a sum of the synchronized first and second drain current signals or obtaining an error signal from a difference between the synchronized first and second drain current signals.

BRIEF DESCRIPTION OF THE DRAWINGS

The above and/or other features and advantages of example embodiments will become apparent by describing in detail example embodiments with reference to the attached drawings. The accompanying drawings are intended to depict example embodiments and should not be interpreted to limit the intended scope of the claims. The accompanying drawings are not to be considered as drawn to scale unless explicitly noted.

DETAILED DESCRIPTION

Figure 1:
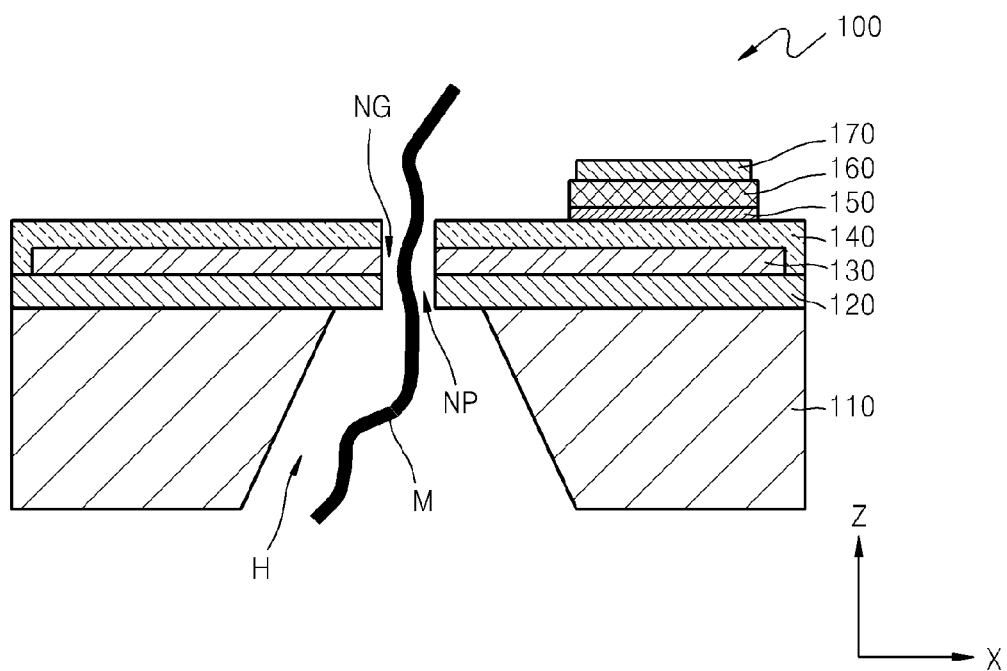
FIG. 1 is a cross-sectional view illustrating a cross-section of a nanogap device according to example embodiments.

Example embodiments will now be described more fully with reference to the accompanying drawings, in which some example embodiments are shown. Example embodiments may, however be embodied in many different forms and should not be construed as being limited to the embodiments set forth herein; rather, these example embodiments are provided so that this disclosure will be thorough and complete, and will fully convey the scope of example embodiments of inventive concepts to those of ordinary skill in the art. In the drawings, the thicknesses of layers and regions are exaggerated for clarity. Like reference numerals in the drawings denote like elements, and thus their description may be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements or layers should be interpreted in a like fashion (e.g., "between" versus "directly between," "adjacent" versus "directly adjacent," "on" versus "directly on". As used herein the term "and/or" includes any and all combinations of one or more of the associated listed items. Expressions such as "at least one of," when preceding a list of elements, modify the entire list of elements and do not modify the individual elements of the list.

It will be understood that, although the terms "first," "second," etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be orientated "above" the other elements or features. Thus, the exemplary term "below" can encompass both an orientation of above and below. The device may be otherwise orientated (rotated 90 degrees or at other orientations) and the spatially relative descriptors used herein interpreted accordingly.

The terminology used herein is for the purpose of describing particular embodiments only and is not intended to limit example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as being limited to the particular shapes of regions illustrated herein and are to include deviations in shapes that result, for example, from manufacturing. For example, an implanted region illustrated as a rectangle will have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Hereinafter, nanogap devices and methods of processing signals from the nanogap devices according to example embodiments will be described more fully with reference to the accompanying drawings.

Figure 2:
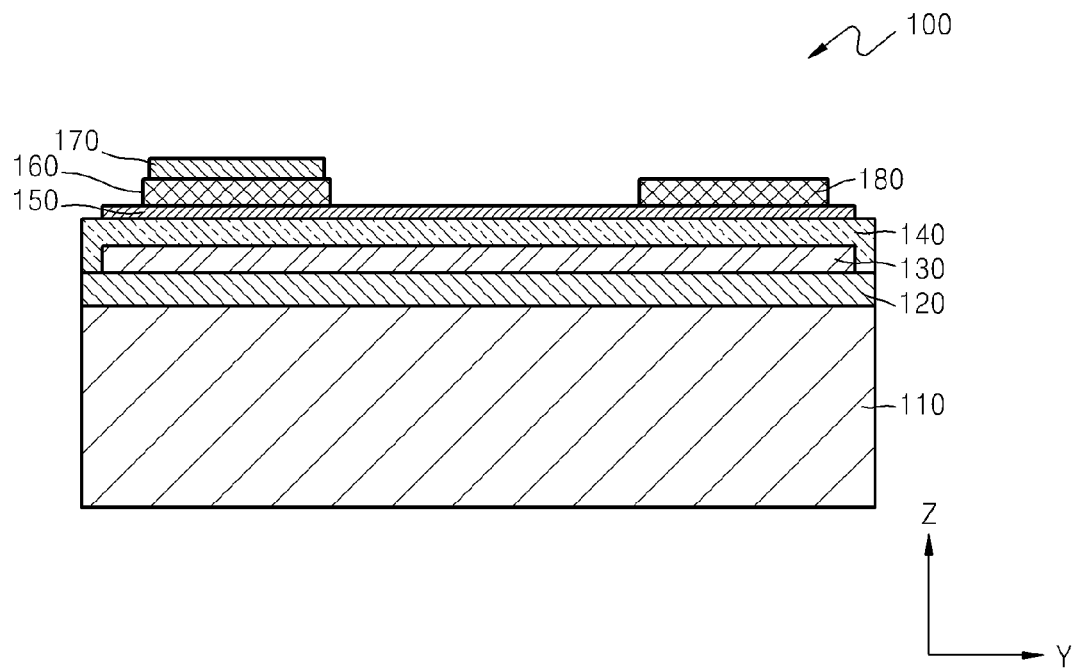
FIG. 2 is a cross-sectional view illustrating another cross-section of the nanogap device of FIG. 1.
Figure 3:
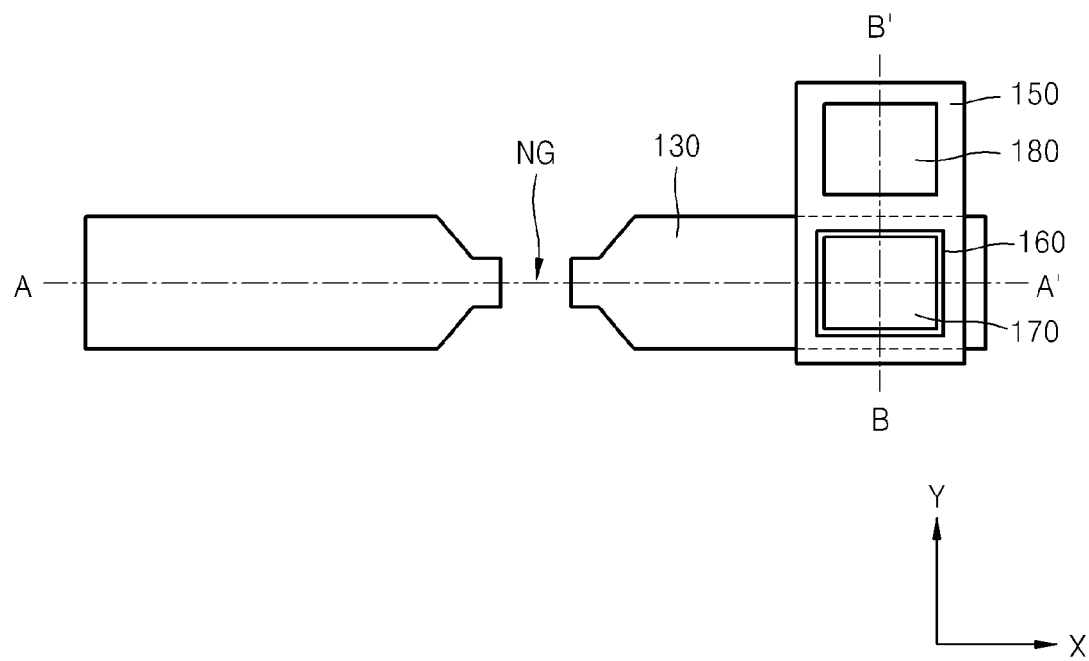
FIG. 3 is a plan view of an arrangement of a first nanogap electrode, a first graphene layer, a first semiconductor layer, a first drain electrode, and a first source electrode of the nanogap device of FIG. 1.

FIG. 1 is a cross-sectional view of a nanogap device 100 according to example embodiments, FIG. 2 is a cross-sectional view illustrating another cross-section of the nanogap device 100 of FIG. 1, and FIG. 3 is a plan view of an arrangement of a first nanogap electrode 130, a first graphene layer 150, a first semiconductor layer 160, a first drain electrode 170, and a first source electrode 180 of the nanogap device 100 of FIG. 1.

Referring to FIGS. 1-3, the nanogap device 100 may include a first insulation layer 120 having a nanopore NP, the first nanogap electrode 130 which may be formed on the first insulation layer 120 and may be divided into two parts having a nanogap NG facing the nanopore NP therebetween, a second insulation layer 140 which may be formed on the first nanogap electrode 130, the first graphene layer 150 which may be formed on the second insulation layer 140, the first semiconductor layer 160 which may be formed on the first graphene layer 150, the first drain electrode 170 which may be formed on the first semiconductor layer 160, and the first source electrode 180 which may be formed on the first graphene layer 150 such as to be apart from the first semiconductor layer 160.

When a target molecule M, for example, a deoxyribonucleic acid (DNA), passes through the nanogap NG, the nanogap device 100 may generate a signal for distinguishing bases that constitute the DNA. According to example embodiments, the nanogap device 100 may have a structure that enables the first nanogap electrode 130 to be used as a gate electrode of a tunable diode which may be formed of the first graphene layer 150 and the first semiconductor layer 160.

A structure and materials of the nanogap device 100 will now be described in detail.

A substrate 110 may support the first insulation layer 120 and the first nanogap electrode 130 which may be formed on the first insulation layer 120, and may have a hole H that faces the nanopore NP which may be formed in the first insulation layer 120. The substrate 110 may be formed of a semiconductor material, a polymer material, or the like. Examples of the semiconductor material may include silicon (Si), germanium (Ge), gallium arsenide (GaAs), and/or gallium nitride (GaN), and examples of the polymer material may include an organic polymer and/or an inorganic polymer. The substrate 110 may be formed of quartz, glass, or the like. The hole H which may be formed in the substrate 110 may have a size of several μm or less, and may have an inclined side surface, and may have a shape that narrows from its entrance to inside. The hole H having this shape may guide the target molecule M so that the target molecule M may easily flow from the bottom of the substrate 110 toward the nanogap NG.

The first insulation layer 120 may be formed of an insulation material, for example, silicon nitride or silicon oxide. For example, SiO2, HfO2, Al2O3, Si3N4, or any mixtures thereof may be used. Alternatively, the first insulation layer 120 may be a multi-layered film including multiple layers respectively formed of the aforementioned materials. The nanopore NP which may be formed in the first insulation layer 120 may be connected to the hole H of the substrate 110. In other words, the nanopore NP may be located to face the hole H. The size of the nanopore NP may be determined in consideration of the size of the target molecule M, which is to be detected. The nanopore NP may be formed using focused ion beam (FIB) equipment.

The first nanogap electrode 130 may be formed of a metal material having high conductivity. The first nanogap electrode 130 may be formed to have a similar thickness to a DNA base, for example, a thickness of about 1 nm or less. The first nanogap electrode 130 may be formed of a graphene material. Graphene is a hexagonal mono-layered structure which may be formed of carbon. The mobility of charge within graphene is high and thus graphene shows similar behavior as a metal having high electrical conductivity. Moreover, the thickness of graphene may be thin, namely, several Å, and thus it may be easy to obtain a nano-sized nanogap capable of measuring a tunneling current change caused by the target molecule M passing through the nanogap NG. The first nanogap electrode 130 may be divided into the two parts having the nanogap NG therebetween, and the width of a portion of the first nanogap electrode 130 that faces the nanogap NG may be less than that of the other portions thereof. This shape may facilitate formation of a small nanogap NG having a size of several nanometers. The nanogap NG may be formed to have a length of 2 nm or less. The length of the nanogap NG may denote a distance between the two parts of the first nanogap electrode 130 that may be separated by the nanogap NG.

Although the nanopore NP and the nanogap NG may have the same size in FIG. 1, this is only an example, and the nanopore NP may have a larger diameter than the nanogap NG. The nanogap NG may be formed using focused FIB equipment.

The second insulation layer 140 may be formed of an insulation material, for example, silicon nitride or silicon oxide. For example, SiO2, HfO2, Al2O3, Si3N4, or any mixtures thereof may be used. Since the first nanogap electrode 130 of the nanogap device 100 may serve as a gate electrode, the second insulation layer 140 may serve as a gate insulation layer. Accordingly, as the second insulation layer 140 becomes thinner, a small change of a gate voltage may be amplified well. The second insulation layer 140 may be formed to have a thickness in the range of about 5 nm to about 20 nm. Here, the thickness of the second insulation layer 140 may denote a distance from an upper surface of the first nanogap electrode 130 and a lower surface of the first graphene layer 150.

The first graphene layer 150 may be formed of a graphene material.

The first semiconductor layer 160 may be formed of any of various sorts of semiconductor materials. Examples of the semiconductor materials may include Si, Ge, a compound semiconductor, such as GaAs, GaN, indium phosphide (InP), gallium phosphide (GaP), and an oxide semiconductor, such as, zinc oxide (ZnO), indium (InO), tin oxide (SnO), indium zinc oxide (InZnO), zinc tin oxide (ZnSnO), or indium tin oxide (InSnO). The first semiconductor layer 160 may be mono-layered or multi-layered.

A graphene/semiconductor structure which may be obtained by stacking a graphene material and a semiconductor material may have the characteristics of a Schottky diode. When a gate voltage is applied to the graphene/semiconductor structure, the graphene/semiconductor structure may serve as a tunable diode of which characteristics may be modulated. According to the nanogap device 100 of example embodiments, the first nanogap electrode 130 may serve as a gate electrode, and an electrical signal which may be generated by the target molecule M passing through the nanogap NG may be amplified.

Figure 4:
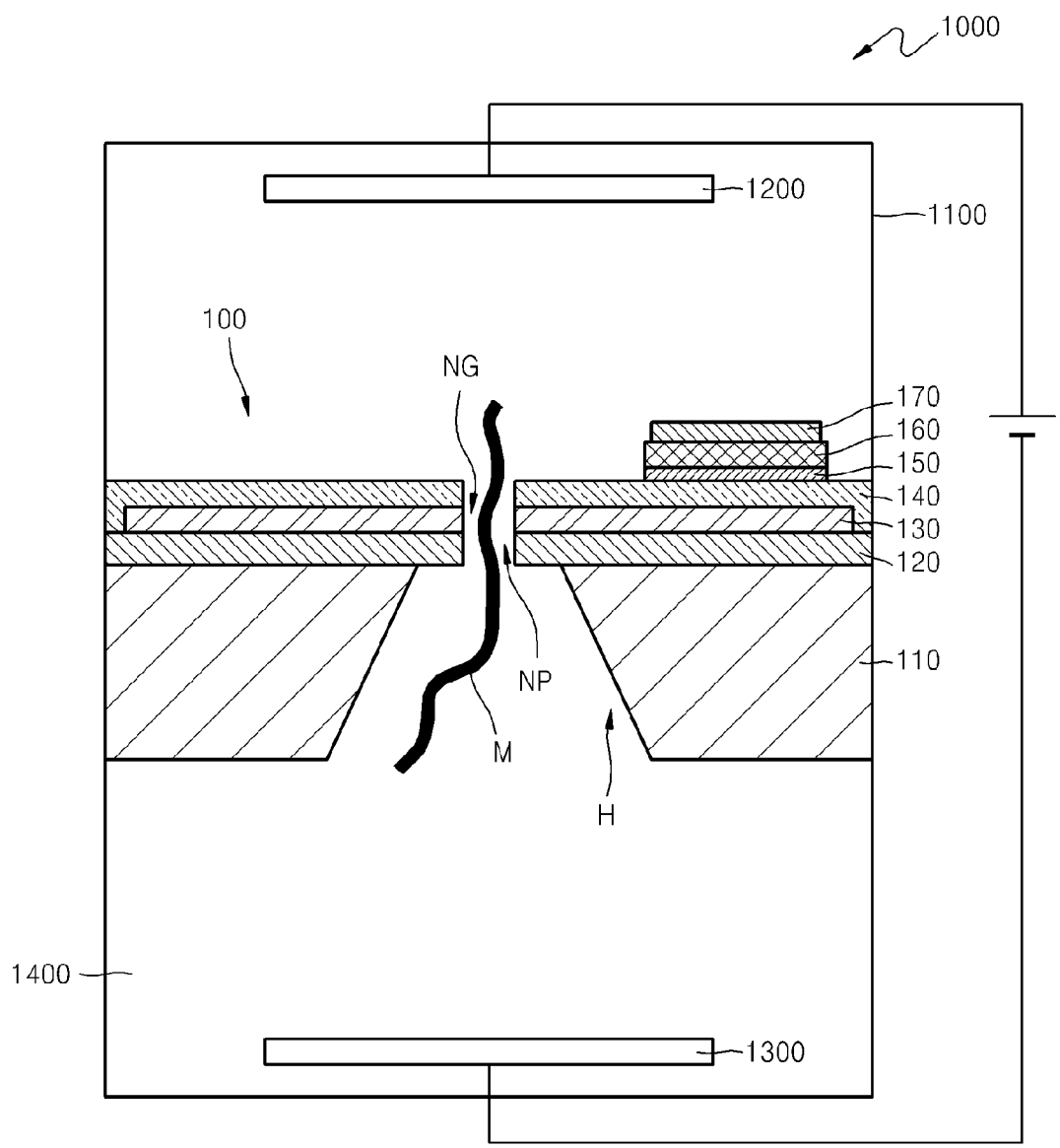
FIG. 4 is a cross-sectional view of a molecule detection apparatus using the nanogap device of FIG. 1, according to example embodiments.

FIG. 4 is a cross-sectional view of a molecule detection apparatus 1000 using the nanogap device 100 of FIG. 1, according to example embodiments.

The molecule detection apparatus 1000 may include the nanogap device 100 of FIG. 1, a water tank 1100 which may contain a sample that may pass through the nanogap, and a first electrode 1200 and a second electrode 1300 which may induce movement of the sample, and may have, for example, a channel structure that may enable a target molecule M within the sample to flow.

The nanogap device 100 may be disposed within the water tank 1100, and the first electrode 1200 and the second electrode 1300 may be respectively disposed in regions over and under the nanogap device 100 to form an electric field within the sample in order to move the target molecule M within the sample. The water tank 1100 may be filled with a buffer solution, such as, water, deionized water, or an electrolyte solution. The buffer solution may be a movement medium for a target molecule that the nanogap device 100 may detect. DNA of a single strand, for example, has a negative charge. When a voltage is applied from an external power source to the first and second electrodes 1200 and 1300, the DNA may move from a region where the second electrode 1300, namely, a negative electrode, may be located to a region where the first electrode 1200, namely, a positive electrode, is located, due to an electric field generated by the applied voltage. In other words, the DNA of a single strand introduced into the region where the second electrode 1300 may be located may be moved near the hole H of the substrate 110 by the electric field applied thereon, and is guided toward the nanopore NP by the hole H. When the DNA of a single strand passes through the nanogap NG via the nanopore NP, an electrical signal change in the nanogap electrode 170 may be measured, and thus the bases of the DNA may be distinguished from one another.

Various other channel structures that may enable the target molecule M to pass through the nanogap NG may be used.

Figure 5:
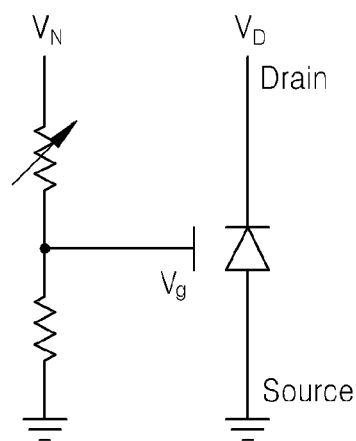
FIG. 5 is a circuit diagram of an equivalent circuit of the nanogap device of FIG. 1.
Figure 6:
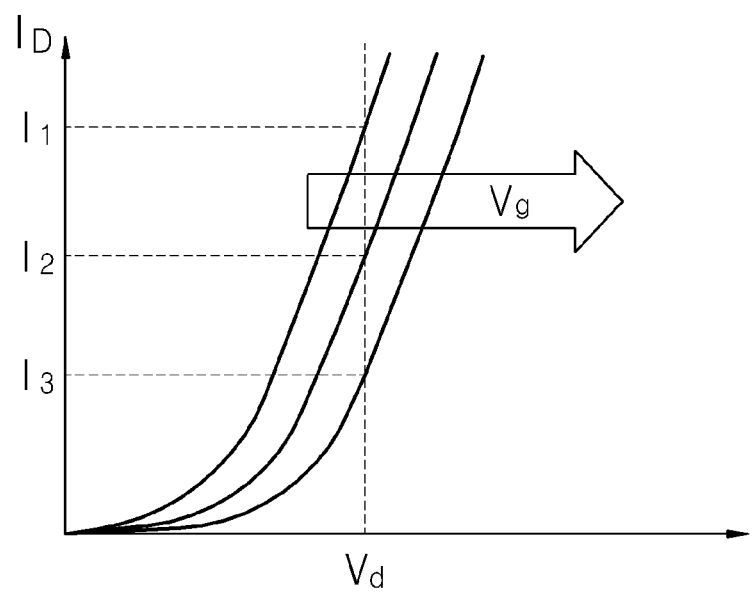
FIG. 6 is a graph showing a drain current versus a voltage of a nanogap electrode that varies according to a molecule that passes through a nanogap of the nanogap device of FIG. 1.

FIG. 5 is a circuit diagram of an equivalent circuit of the nanogap device 100 of FIG. 1, and FIG. 6 is a graph showing a drain current ID versus a voltage of the first nanogap electrode 130 that varies according to the target molecule M that may pass through the nanogap NG of the nanogap device 100 of FIG. 1.

In the equivalent circuit of FIG. 5, a variable resistance is caused by the target molecule M that passes through the nanogap NG. The value of the variable resistance may vary depending on the type of base that may be included in the target molecule M, and a gate voltage $V_g$ varies accordingly. The gate voltage $V_g$, varying as described above, is detected as an amplified drain current signal, namely, the drain current $I_D$, as illustrated in FIG. 6.

Figure 7:
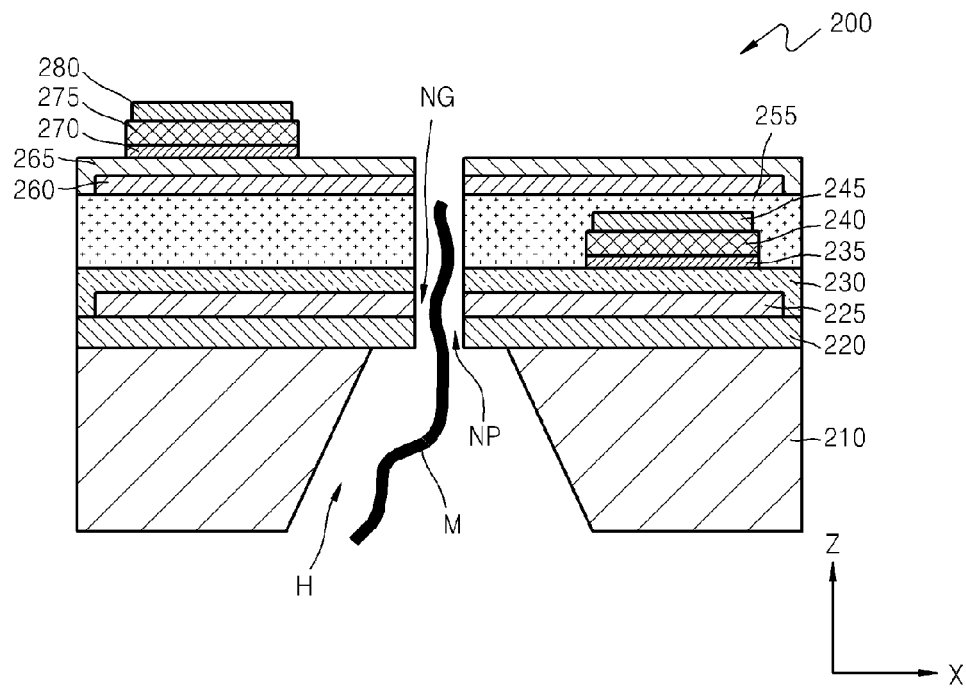
FIG. 7 is a cross-sectional view of a nanogap device according to example embodiments.
Figure 8:
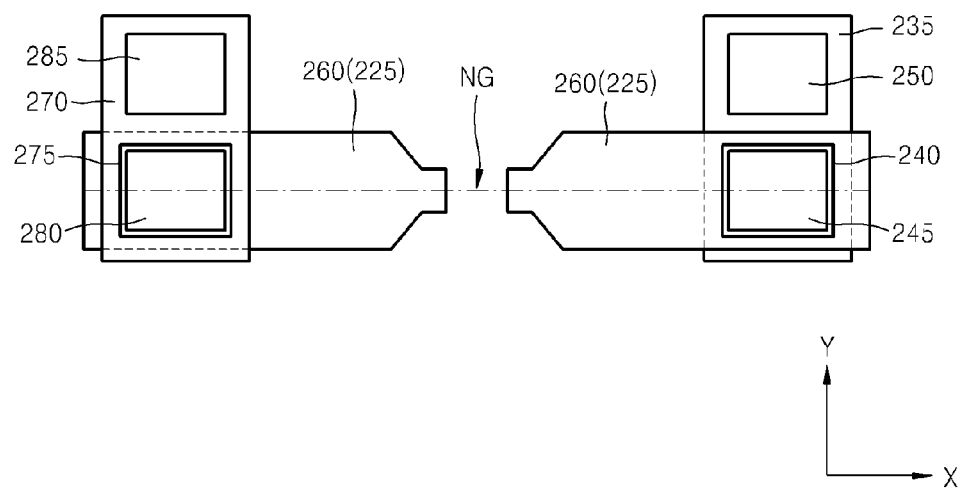
FIG. 8 is a plan view of an arrangement of a first nanogap electrode, a second nanogap electrode, a first graphene layer, a second graphene layer, a first semiconductor layer, a second semiconductor layer, a first drain electrode, a second drain electrode, a first source electrode, and a second source electrode of the nanogap device of FIG. 7.

FIG. 7 is a cross-sectional view of a nanogap device 200 according to example embodiments, and FIG. 8 is a plan view of an arrangement of a first nanogap electrode 225, a second nanogap electrode 260, a first graphene layer 235, a second graphene layer 270, a first semiconductor layer 240, a second semiconductor layer 275, a first drain electrode 245, a second drain electrode 280, a first source electrode 250, and a second source electrode 285 of the nanogap device 200 of FIG. 7.

Referring to FIGS. 7 and 8, the nanogap device 200 may include a first insulation layer 220 having a nanopore NP, a first nanogap electrode 225 that may be formed on a first insulation layer 220 and may be divided into two parts which may have a nanogap NG facing the nanopore NP therebetween, a second insulation layer 230 which may be formed on the first nanogap electrode 225, a first graphene layer 235 which may be formed on the second insulation layer 230, a first semiconductor layer 240 which may be formed on the first graphene layer 235, a first drain electrode 245 which may be formed on the first semiconductor layer 240, and a first source electrode 250 which may be formed on the first graphene layer 235 such as to be apart from the first semiconductor layer 240. The nanogap device 200 may further include a protection layer 255 which may be formed to cover the first graphene layer 235, the first semiconductor layer 240, and the first drain electrode 245, the second nanogap electrode 260 which may be formed on the protection layer 255 and which may include two parts separated by the nanogap NG, a third insulation layer 265 which may be formed on the second nanogap electrode 260, the second graphene layer 270 which may be formed on the third insulation layer 265, the second semiconductor layer 275 which may be formed on the second graphene layer 270, the second drain electrode 280 which may be formed on the second semiconductor layer 275, and/or the second source electrode 285 which may be formed on the second graphene layer 270 such as to be apart from the second drain electrode 280.

The nanogap device 200 according to example embodiments may be obtained by adding the second nanogap electrode 260, the second graphene layer 270, and/or the second semiconductor layer 275 to the nanogap device 100 of FIG. 1, and the second nanogap electrode 260 which may serve as a gate electrode with respect to a diode which may be formed of the second graphene layer 270 and the second semiconductor layer 275.

The first nanogap electrode 225, the first graphene layer 235, the first semiconductor layer 240, the first drain electrode 245, the first source electrode 250, the first insulation layer 220, and the second insulation layer 230 are substantially the same as the elements having identical names in FIG. 1. Therefore, a detailed description thereof will be omitted. The structures and materials of the second nanogap electrode 260, the second graphene layer 270, the second semiconductor layer 275, the second drain electrode 280, the second source electrode 285, and the third insulation layer 265 may refer to the above-illustrated structures and materials of the first nanogap electrode 130, the first graphene layer 150, the first semiconductor layer 160, the first drain electrode 170, the first source electrode 180, and the second insulation layer 140 of FIG. 1, respectively.

A drain current $I_D$ may be repeatedly obtained from the nanogap device 200, with a time delay corresponding to a distance between the first nanogap electrode 225 and the second nanogap electrode 260.

Figure 9A:
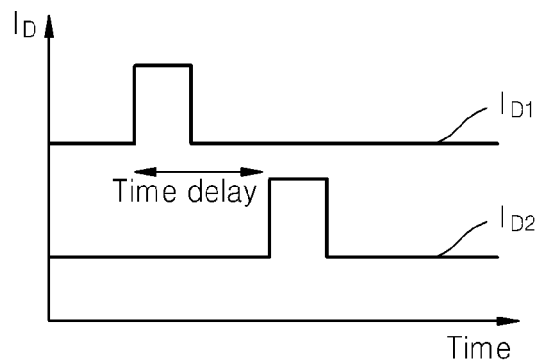
FIGS. 9A and 9B are drain current graphs for describing a method of analyzing a signal from the nanogap device of FIG. 9.
Figure 9B:
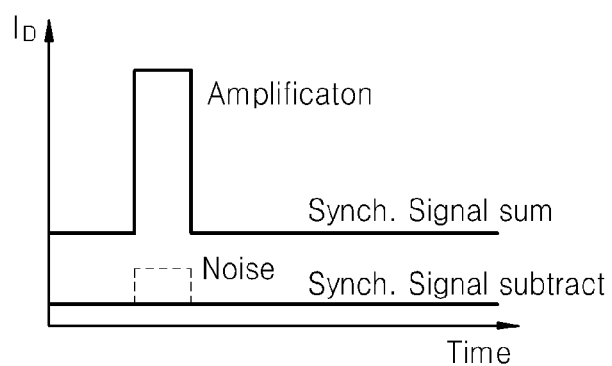

FIGS. 9A and 9B are drain current graphs for describing a method of analyzing a signal from the nanogap device 200 of FIG. 7.

Referring to FIG. 9A, a first drain current signal $I_{D1}$ between the first drain electrode 245 and the first source electrode 250 and a second drain current signal $I_{D2}$ between the second drain electrode 280 and the second source electrode 285 may be measured with time.

The first drain current signal $I_{D1}$ and the second drain current signal $I_{D2}$ may be synchronized with each other and may be used in signal amplification or detection of an error signal. For example, as illustrated in FIG. 9B, an amplification signal Amplification may be obtained from a signal of Synch. Signal sum corresponding to a sum of the first drain current signal $I_{D1}$ and the second drain current signal $I_{D2}$ synchronized with each other, and an error signal Noise may be obtained from a signal of Synch. Signal subtract corresponding to a difference between the first drain current signal $I_{D1}$ and the second drain current signal $I_{D2}$ synchronized with each other.

Although this signal processing has been described above by referring to the structure of the nanogap device 200 of FIG. 7, the signal processing may be performed with a plurality of nanogap devices 100 of FIG. 1 arranged so that their respective nanogaps NG face each other. In other words, a drain current signal between the first drain electrode 170 and the first source electrode 180 of each of a plurality of nanogap devices 100 may be measured with time, the respective drain current signals of the nanogap devices 100 may be synchronized with each other, and then an amplification signal or an error signal may be obtained using a sum of or a difference between the synchronized drain current signals.

FIGS. 10A through 10H are cross-sectional views for explaining a method of manufacturing a nanogap device 300, according to example embodiments.

Figure 10A:
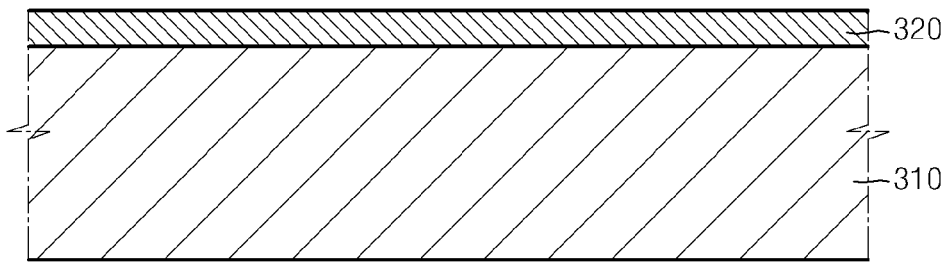
FIGS. 10A through 10H are cross-sectional views for explaining a method of manufacturing a nanogap device, according to example embodiments.
Figure 10A:
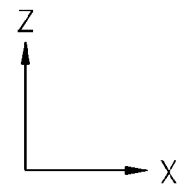

Referring to FIG. 10A, a first insulation layer 320 may be formed on a substrate 310. Semiconductor substrates or polymer substrates formed of various materials may be used as the substrate 310. For example, a silicon substrate may be polished by chemical mechanical polishing (CMP) or the like to have a thickness of about 300 um, thereby forming the substrate 310. Although not illustrated in FIGS. 10A through 10H, an etch mask layer for forming a desired (and/or predetermined) hole may be further formed on a lower surface of the substrate 310. The first insulation layer 320 may be formed of an insulation material, for example, silicon nitride or silicon oxide, by deposition or the like.

Figure 10B:
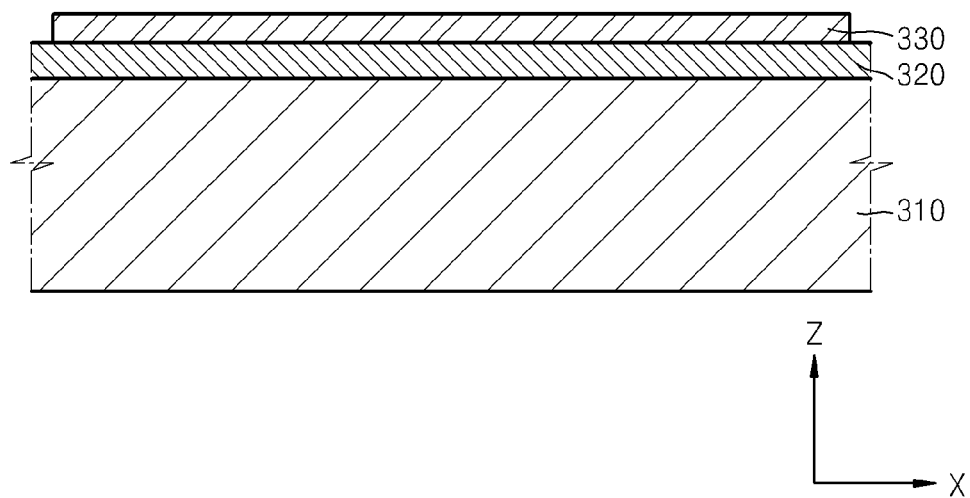
Figure 10C:
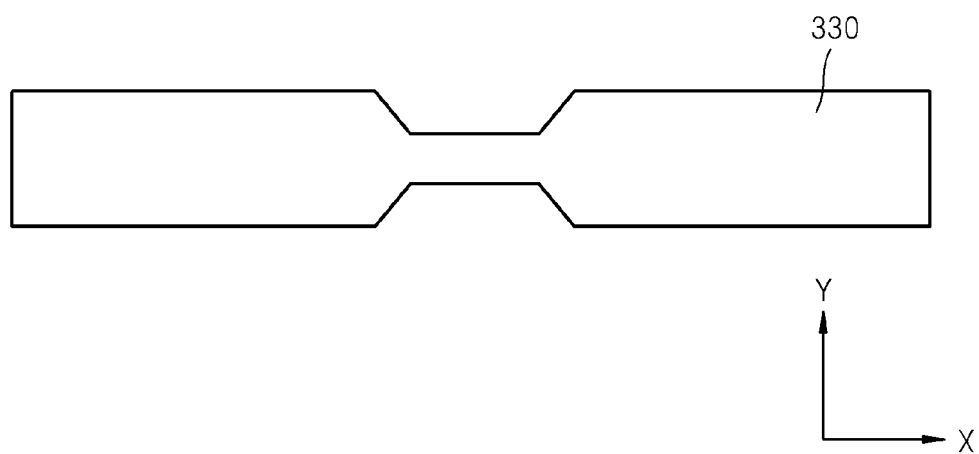

Next, as illustrated in FIG. 10B, a first nanogap electrode 330 may be formed on the first insulation layer 320. The first nanogap electrode 330 may be patterned to have a shape as illustrated in FIG. 10C. The first nanogap electrode 330 may be formed of a metal material or a graphene material.

Figure 10D:
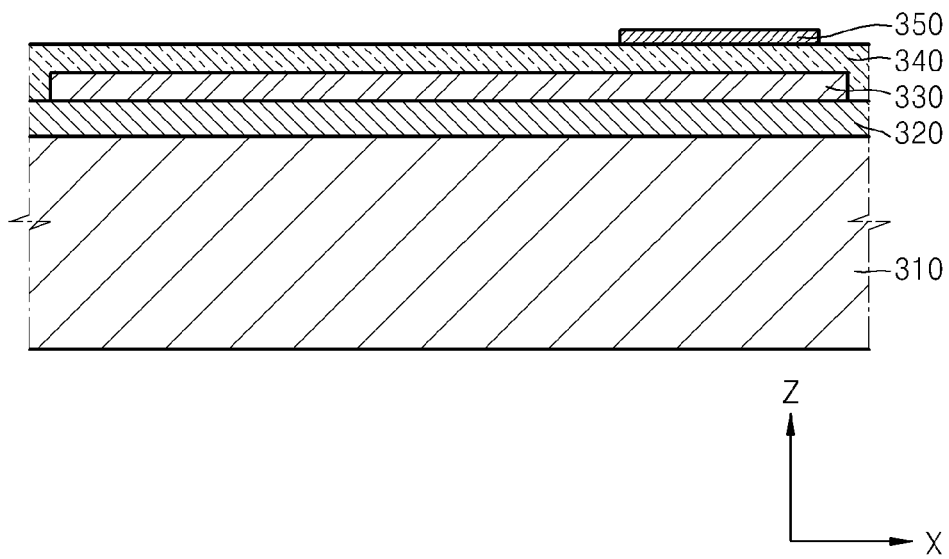

Thereafter, as illustrated in FIG. 10D, a second insulation layer 340 that may cover the first nanogap electrode 330 may be formed, and a first graphene layer 350 may be formed on the second insulation layer 340. The second insulation layer 340 may be formed of an insulation material, for example, silicon nitride or silicon oxide, by deposition or the like. The first graphene layer 350 may be formed of a graphene material and may be synthesized by chemical vapor deposition (CVD). For example, the first graphene layer 350 may be synthesized on another substrate by CVD and then may be transferred onto the second insulation layer 340. Alternatively, the first graphene layer 350 may be obtained by using a silicon carbide (SiC) crystal pyrolysis method, or a micromechanical method, that is, a method of attaching a sticky tape to a graphite sample, detaching the sticky tape therefrom so that graphene may be separated from the graphite sample and adsorbed onto the surface of the sticky tape, and transferring the graphene onto the second insulation layer 340.

Figure 10E:
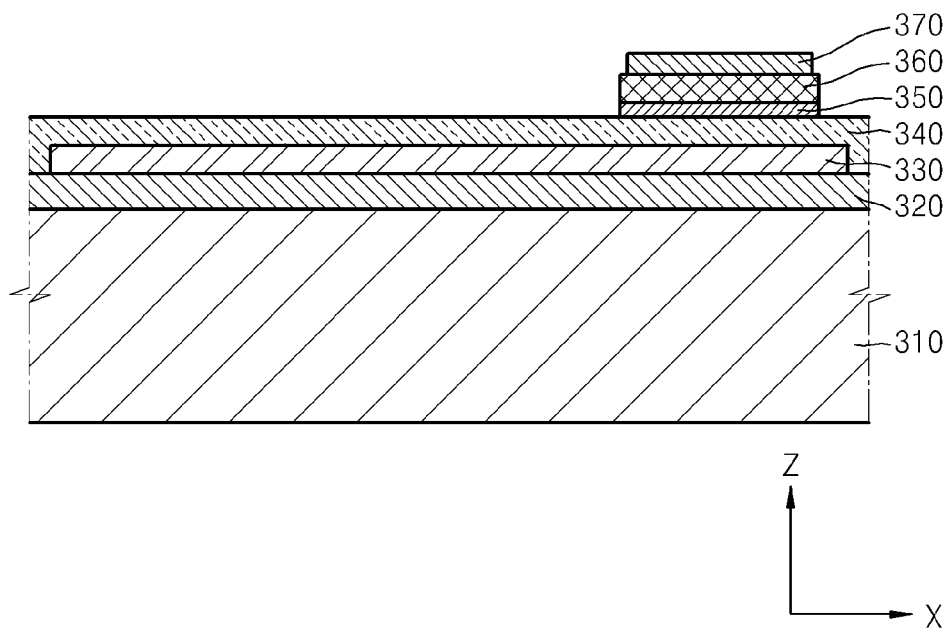
Figure 10F:
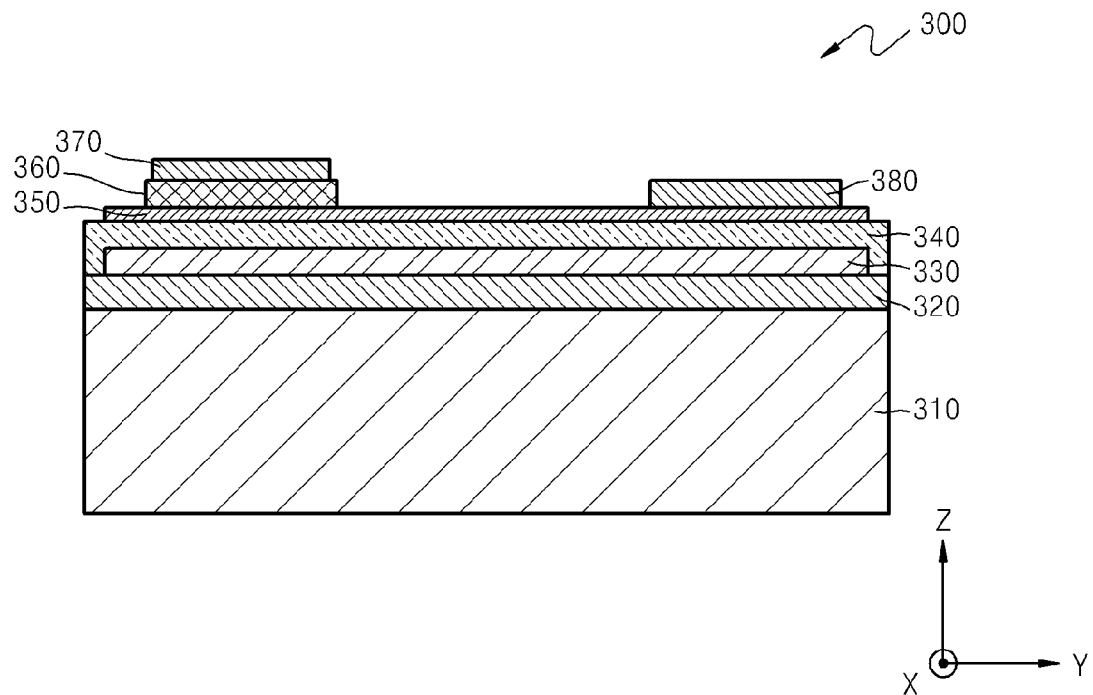

Then, referring to FIGS. 10E and 10F, a first semiconductor layer 360 may be formed on the first graphene layer 350, a first drain electrode 370 may be formed on the first semiconductor layer 360, and a first source electrode 380 may be formed on the first graphene layer 350 such as to be apart from the first semiconductor layer 360. The cross-section of FIG. 10F is different from the cross-section of FIG. 10E.

The first semiconductor layer 360 may be formed of any of various sorts of semiconductor materials. For example, the first semiconductor layer 360 may be formed of Si, Ge, a compound semiconductor, such as GaAs or GaN, or an oxide semiconductor, such as, zinc oxide (ZnO), indium (InO), tin oxide (SnO), indium zinc oxide (InZnO), zinc tin oxide (ZnSnO), or indium tin oxide (InSnO).

The first drain electrode 370 and the first source electrode 380 may be formed by depositing a metal material having high electrical conductivity, for example, platinum (Pt), ruthenium (Ru), gold (Au), silver (Ag), molybdenum (Mo), aluminum (Al), tungsten (W), or copper (Cu).

Figure 10G:
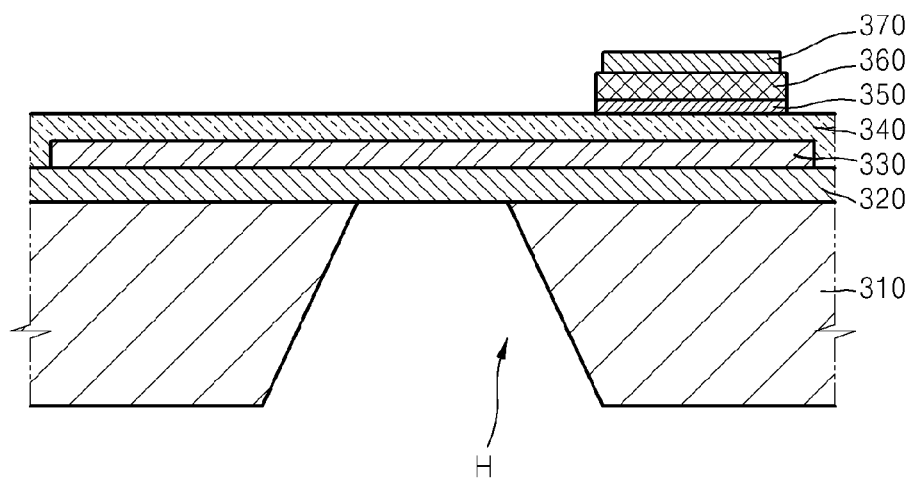

Then, as illustrated in FIG. 10G, the lower surface of the substrate 310 may be anisotropically etched to form a hole H.

Figure 10H:
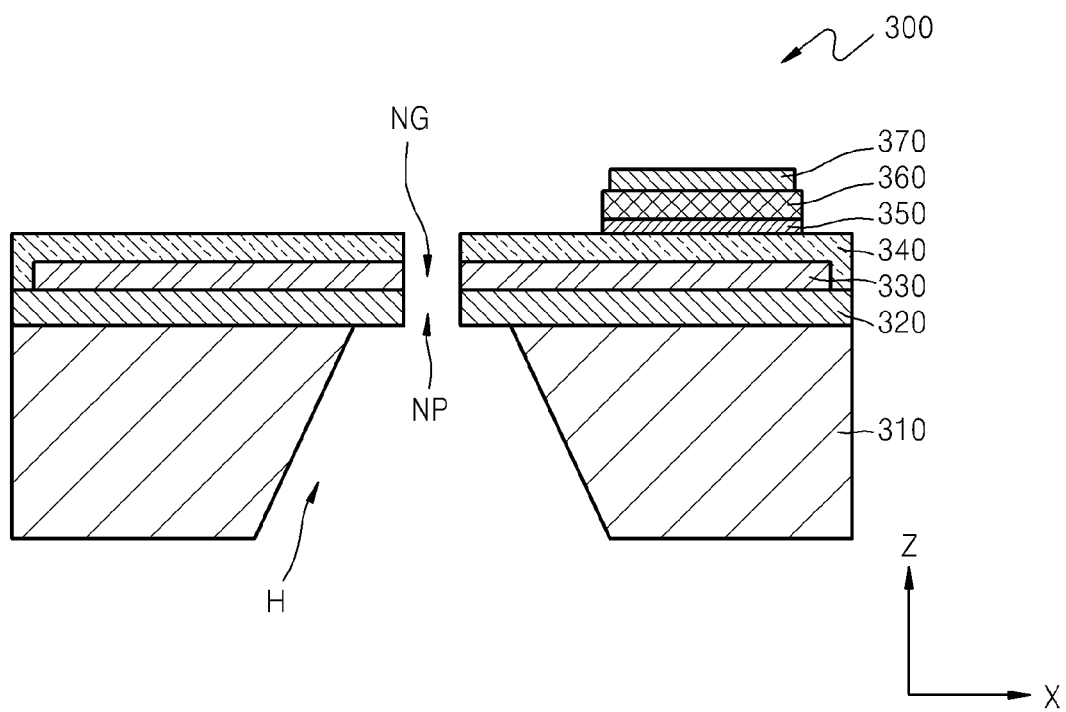

Next, as illustrated in FIG. 10H, a nanopore NP and a nanogap NG are formed. The nanopore NP and the nanogap NG may be formed to communicate with the hole H, by using FIB equipment or transmission electron microscope (TEM) equipment. Although the nanopore NP and the nanogap NG have the same size in FIG. 10H, this is only an example, and the nanopore NP may be larger than the nanogap NG.

Although it is illustrated in FIG. 10H that the nanogap device 300 manufactured in this way has a similar structure to the nanogap device 100 of FIG. 1, the nanogap device 300 may be manufactured to include two layers of nanogap electrodes as illustrated in FIG. 7 by repeating similar process operations.

Since a nanogap device as described above has a structure that enables a nanogap electrode to be used as a gate electrode of a tunable diode, a small electrical signal in the nanogap electrode may be amplified.

Alternatively, the nanogap device as described above may have a structure obtained by repeatedly stacking a nanogap electrode and a diode formed of graphene and semiconductor, and two signals may be obtained from this structure and may be used in base analysis.

According to a method of processing a signal from a nanogap device as described above, repetitive measurements may be performed on the same base at regular intervals, and results of the measurements may be synchronized with each other to obtain an amplification signal or an error signal.

It should be understood that example embodiments having thus been described should be considered in a descriptive sense only and not for purposes of limitation. Descriptions of features or aspects within each nanogap device according to example embodiments should typically be considered as available for other similar features or aspects in other nanogap devices according to example embodiments. For example, one skilled in the art knows that the structure of the nanogap devices and the methods of processing signals from the nanogap devices shown in FIGS. 1 through 10H may be variously modified. Therefore, while some example embodiments have been particularly shown and described, it will be understood by one of ordinary skill in the art that variations in form and detail made therein are not to be regarded as a departure from the intended spirit and scope of example embodiments, and all such modifications as would be obvious to one skilled in the art are intended to be included within the scope of the following claims.

What is claimed is:

1. A nanogap device comprising:
   a first insulation layer having a nanopore therein;
   a first nanogap electrode on the first insulation layer and divided into two parts with a nanogap interposed between the two parts, the nanogap facing the nanopore;
   a second insulation layer on the first nanogap electrode;
   a first graphene layer on the second insulation layer;
   a first semiconductor layer on the first graphene layer;
   a first drain electrode on the first semiconductor layer; and
   a first source electrode on the first graphene layer apart from the first semiconductor layer.

2. The nanogap device of claim 1, wherein portions of the two parts of the first nanogap electrode that face the nanogap are narrower than other portions.

3. The nanogap device of claim 1, wherein a thickness of the first nanogap electrode is 1 nm or less.

4. The nanogap device of claim 1, wherein a length of the nanogap of the first nanogap electrode is 2 nm or less.

5. The nanogap device of claim 1, wherein the first nanogap electrode includes a graphene material.

6. The nanogap device of claim 1, further comprising:
   a first protection layer that covers the first graphene layer, the first semiconductor layer, and the first drain electrode;
   a second nanogap electrode on the first protection layer and divided into two parts with a nanogap facing the nanopore and interposed between the two parts;
   a third insulation layer on the second nanogap electrode;
   a second graphene layer on the second insulation layer;
   a second semiconductor layer on the second graphene layer;

a second drain electrode on the second semiconductor layer; and a second source electrode on the second graphene layer such as to be apart from the second drain electrode.

7. The nanogap device of claim 6, wherein portions of the two parts of the second nanogap electrode that face the nanogap are narrower than other portions.

8. The nanogap device of claim 6, wherein a thickness of the second nanogap electrode is 1 nm or less.

9. The nanogap device of claim 6, wherein a length of the nanogap of the second nanogap electrode is 2 nm or less.

10. The nanogap device of claim 6, wherein the second nanogap electrode includes a graphene material.

11. The nanogap device of claim 1, further comprising:
a substrate having a hole formed therein,
wherein the first insulation layer is on the substrate so that the nanopore faces the hole.

12. The nanogap device of claim 11, wherein the hole has an inclined side surface and narrows from an entrance to inside.

13. A method of processing a signal from a nanogap device, the method comprising:
arranging a plurality of the nanogap devices of claim 1 such that respective nanogaps of the plurality of nanogap devices face one another;
measuring a drain current signal between the first drain electrode and the first source electrode of each of the plurality of nanogap devices according to time; and
synchronizing the respective drain current signals of the plurality of nanogap devices with one another.

14. The method of claim 13, further comprising:
summing the synchronized drain current signals of the plurality of nanogap devices to obtain an amplification signal.

15. The method of claim 13, further comprising:
obtaining an error signal from a difference between the synchronized drain current signals of the plurality of nanogap devices.

16. A method of processing a signal from the nanogap device of claim 6, the method comprising:
measuring a first drain current signal between the first drain electrode and the first source electrode according to time; and
measuring a second drain current signal between the second drain electrode and the second source electrode according to time.

17. The method of claim 16, further comprising:
synchronizing the first drain current signal with the second drain current signal.

18. The method of claim 17, further comprising:
obtaining an amplification signal from a sum of the first and second drain current signals synchronized with each other.

19. The method of claim 18, further comprising:
obtaining an error signal from a difference between the first and second drain current signals synchronized with each other.

* * * * *